(12) United States Patent
Baumbach et al.

(10) Patent No.: US 12,144,945 B2
(45) Date of Patent: Nov. 19, 2024

(54) BALLOON CATHETER SYSTEMS FOR DELIVERY OF DRY DRUG DELIVERY VESICLES TO A VESSEL IN THE BODY

(71) Applicant: Caliber Therapeutics, LLC, New Hope, PA (US)

(72) Inventors: William R. Baumbach, New Hope, PA (US); Darren R. Sherman, New Hope, PA (US); Robert S. Burgermeister, New Hope, PA (US)

(73) Assignee: Caliber Therapeutics, LLC, New Hope, PA (US)

( * ) Notice: Subject to any disclaimer, the term of this patent is extended or adjusted under 35 U.S.C. 154(b) by 17 days.

(21) Appl. No.: 18/110,041

(22) Filed: Feb. 15, 2023

(65) Prior Publication Data

US 2023/0191090 A1 Jun. 22, 2023

Related U.S. Application Data

(60) Continuation of application No. 17/075,080, filed on Oct. 20, 2020, now abandoned, which is a
(Continued)

(51) Int. Cl.
*A61M 25/10* (2013.01)
*A61K 9/107* (2006.01)
(Continued)

(52) U.S. Cl.
CPC ......... *A61M 25/1018* (2013.01); *A61K 9/107* (2013.01); *A61K 31/00* (2013.01);
(Continued)

(58) Field of Classification Search
CPC ............ A61M 5/1407; A61M 5/16827; A61M 25/1018–10188; A61M 25/104;
(Continued)

(56) References Cited

U.S. PATENT DOCUMENTS

| 4,403,612 A | 9/1983 | Fogarty |
| 4,423,725 A | 1/1984 | Baran et al. |

(Continued)

FOREIGN PATENT DOCUMENTS

| EP | 0399712 | 11/1990 |
| EP | 1604704 | 12/2005 |

(Continued)

OTHER PUBLICATIONS

Examination Report dated Sep. 2, 2019 from Australian Patent Application No. 2019202994.
(Continued)

*Primary Examiner* — Kami A Bosworth
(74) *Attorney, Agent, or Firm* — Crockett & Crockett, PC; K. David Crockett, Esq.

(57) ABSTRACT

Devices and methods for balloon delivery of rapamycin and other hydrophobic compounds to the wall of blood vessels. Balloon catheters, such as those used for stent deployment, are modified with the addition of a reservoir of dry micelles. The micelle preparation is reconstituted and the micelles are mobilized when the aqueous solution used to inflate the balloons is injected into the catheter. The micelles are infused into tissue surrounding the balloon when pressurized fluid within the balloon leaks through the wall of the balloon.

7 Claims, 7 Drawing Sheets

Related U.S. Application Data continuation of application No. 16/115,467, filed on Aug. 28, 2018, now Pat. No. 10,806,909, which is a continuation of application No. 15/594,055, filed on May 12, 2017, now Pat. No. 10,207,084, which is a continuation of application No. 15/078,940, filed on Mar. 23, 2016, now Pat. No. 9,649,479, which is a continuation of application No. 14/247,057, filed on Apr. 7, 2014, now Pat. No. 9,649,478, which is a continuation of application No. 12/982,760, filed on Dec. 30, 2010, now Pat. No. 8,696,644, said application No. 14/247,057 is a division of application No. 13/855,653, filed on Apr. 2, 2013, now Pat. No. 8,715,230, which is a continuation of application No. 12/982,760, filed on Dec. 30, 2010, now Pat. No. 8,696,644.

(60) Provisional application No. 61/291,345, filed on Dec. 30, 2009.

(51) Int. Cl.
    *A61K 31/00*     (2006.01)
    *A61K 31/436*     (2006.01)
    *A61L 29/14*     (2006.01)
    *A61L 29/16*     (2006.01)

(52) U.S. Cl.
    CPC .......... *A61K 31/436* (2013.01); *A61L 29/146* (2013.01); *A61L 29/16* (2013.01); *A61M 25/10* (2013.01); *A61M 25/1011* (2013.01); *A61M 25/10182* (2013.11); *A61M 25/10185* (2013.11); *A61M 25/10187* (2013.11); *A61M 25/104* (2013.01); *A61L 2300/416* (2013.01); *A61L 2300/626* (2013.01); *A61M 2025/1013* (2013.01); *A61M 2025/105* (2013.01); *A61M 2025/1075* (2013.01)

(58) Field of Classification Search
    CPC .... A61M 2025/102; A61M 2025/1022; A61M 2025/105; A61J 1/20; A61J 1/2089; A61J 1/2093; A61J 1/2096; A61J 1/22; A61K 8/0291; A61K 9/107; A61K 9/1075; A61K 47/6907; A61K 47/6909; A61K 49/0082; A61K 49/0466; A61K 49/1809; A61K 49/227; A61K 51/1227
    See application file for complete search history.

(56) References Cited

U.S. PATENT DOCUMENTS

| | | |
|---|---|---|
| 5,087,244 A | 2/1992 | Wolinsky et al. |
| 5,120,322 A | 6/1992 | Davis et al. |
| 5,213,576 A | 5/1993 | Abiuso et al. |
| 5,292,321 A | 3/1994 | Lee |
| 5,409,483 A | 4/1995 | Campbell et al. |
| 5,514,092 A | 5/1996 | Forman et al. |
| 6,544,223 B1 | 4/2003 | Kokish |
| 6,706,013 B1 | 3/2004 | Bhat et al. |
| 6,954,977 B2 | 10/2005 | Maguire et al. |
| 7,189,227 B2 | 3/2007 | Lafontaine |
| 8,157,851 B2 | 4/2012 | Andreas |
| 8,414,526 B2 | 4/2013 | Wang |
| 8,696,644 B2 | 4/2014 | Baumbach et al. |
| 8,715,230 B2 | 5/2014 | Baumbach et al. |
| 9,649,478 B2 | 5/2017 | Baumbach et al. |
| 9,649,479 B2 | 5/2017 | Baumbach et al. |
| 10,207,084 B2 | 2/2019 | Baumbach et al. |
| 10,806,909 B2 | 10/2020 | Baumbach et al. |
| 2002/0032406 A1 | 3/2002 | Kusleika |
| 2002/0045856 A1 | 4/2002 | Jaafar et al. |
| 2002/0095114 A1 | 7/2002 | Palasis |
| 2003/0028210 A1 | 2/2003 | Boyle et al. |
| 2003/0036725 A1 | 2/2003 | Lavi et al. |
| 2004/0064094 A1 | 4/2004 | Freyman |
| 2004/0087902 A1 | 5/2004 | Richter |
| 2004/0197409 A1 | 10/2004 | Lyer et al. |
| 2004/0210289 A1 | 10/2004 | Wang et al. |
| 2004/0220511 A1 | 11/2004 | Scott et al. |
| 2004/0236278 A1 | 11/2004 | Herweck et al. |
| 2004/0236279 A1 | 11/2004 | Herwick et al. |
| 2004/0259840 A1 | 12/2004 | Hermann et al. |
| 2004/0260239 A1 | 12/2004 | Kusleika |
| 2004/0267355 A1 | 12/2004 | Scott et al. |
| 2005/0015048 A1 | 1/2005 | Chiu et al. |
| 2005/0107870 A1 | 5/2005 | Wang et al. |
| 2005/0113687 A1 | 5/2005 | Herweck et al. |
| 2005/0158272 A1 | 7/2005 | Whirley et al. |
| 2005/0197622 A1 | 9/2005 | Blumenthal et al. |
| 2005/0245906 A1 | 11/2005 | Makower et al. |
| 2006/0106361 A1 | 5/2006 | Muni et al. |
| 2006/0251710 A1 | 11/2006 | Kwon et al. |
| 2007/0088252 A1 | 4/2007 | Pestotnik et al. |
| 2007/0173785 A1 | 7/2007 | Ostroot |
| 2008/0103478 A1 | 5/2008 | Chiu et al. |
| 2008/0118544 A1 | 5/2008 | Wang |
| 2008/0146489 A1 | 6/2008 | Pacetti et al. |
| 2008/0249461 A1 | 10/2008 | Foreman et al. |
| 2008/0255509 A1 | 10/2008 | Wang |
| 2008/0255510 A1 | 10/2008 | Wang |
| 2008/0276935 A1 | 11/2008 | Wang |
| 2008/0300573 A1 | 12/2008 | Consigny et al. |
| 2008/0300610 A1 | 12/2008 | Chambers |
| 2009/0105686 A1 | 4/2009 | Snow et al. |
| 2009/0198216 A1 | 8/2009 | Muni et al. |
| 2010/0010470 A1 | 1/2010 | Bates |
| 2010/0168714 A1 | 7/2010 | Burke et al. |
| 2010/0185146 A1 | 7/2010 | Ramzipoor et al. |
| 2011/0060276 A1 | 3/2011 | Schaeffer et al. |
| 2011/0160575 A1 | 6/2011 | Beyar et al. |
| 2011/0166547 A1 | 7/2011 | Baumbach et al. |

FOREIGN PATENT DOCUMENTS

| | | |
|---|---|---|
| JP | 2008137975 | 6/2008 |
| WO | WO2006110862 | 10/2006 |
| WO | WO2006114783 | 11/2006 |
| WO | WO2007111636 | 10/2007 |
| WO | WO2008109114 | 9/2008 |
| WO | WO2009036135 | 3/2009 |
| WO | WO2010026578 | 3/2010 |

OTHER PUBLICATIONS

Examination Report dated Feb. 13, 2018 from Australian Patent Application No. 2017225072.
Examination Report dated Jan. 9, 2020 from Australian Patent Application No. 2019202994.
Office Action dated Jul. 28, 2015 from Australian counterpart patent application No. 2014202452.
Office Action dated May 7, 2013 from U.S. Appl. No. 12/982,760.
Examination Report dated Apr. 30. 2019 from Indian Patent Application No. 6116/DELNP/2012.
Examiner's Report dated Feb. 24, 2021 from Canadian Patent Application 3065396.
Extended European Search Report dated Apr. 28, 2021 from European Patent Application No. 20205625.5.
Examination Report dated Jun. 30, 2021 from Australian Patent Application No. 2020281081.
Notice of Hearing dated Mar. 12, 2024 from Indian Patent Application No. 202118051957.
Office Action dated May 13, 2024 from European Patent Application No. 20205625.5.

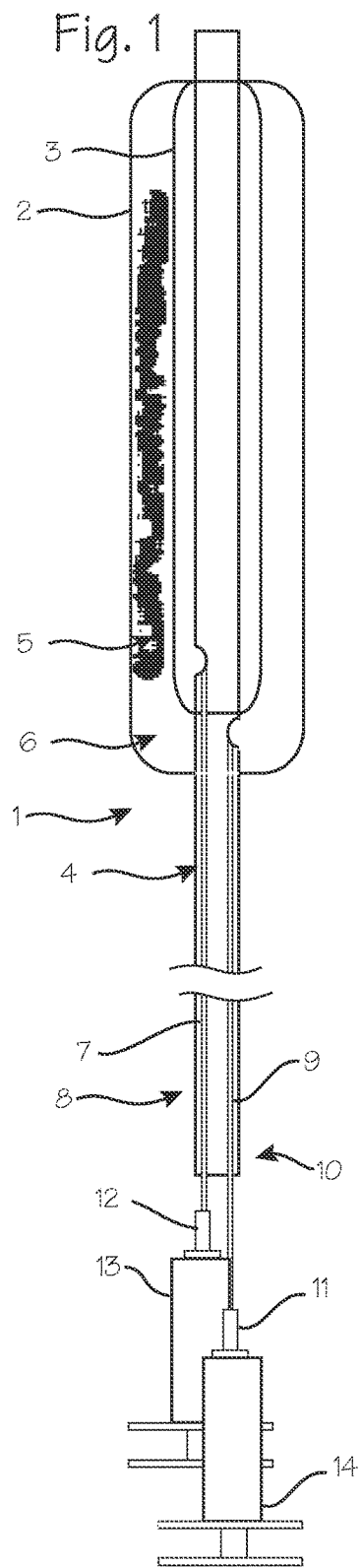
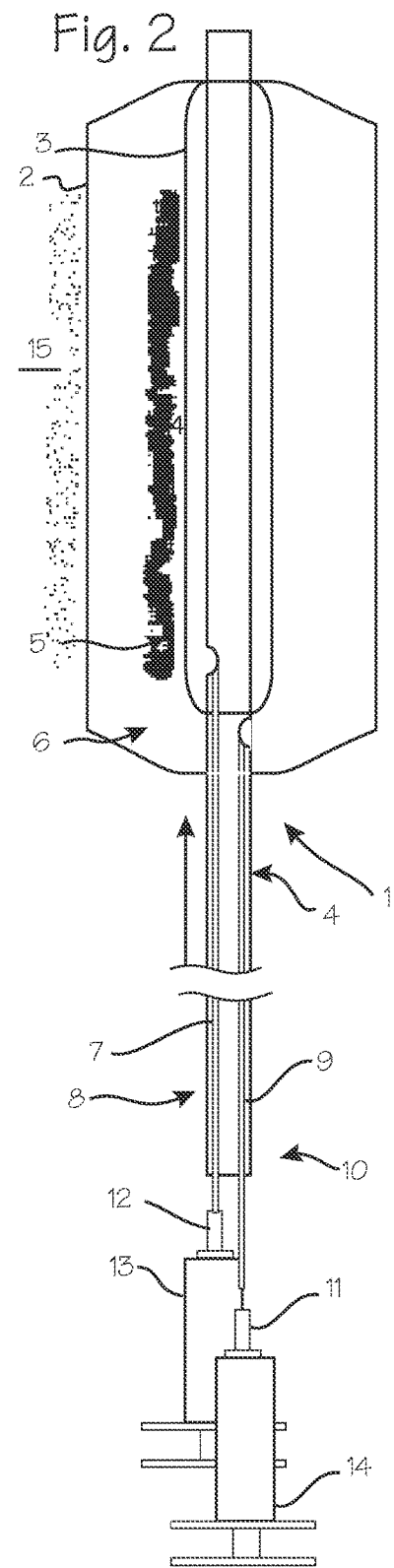
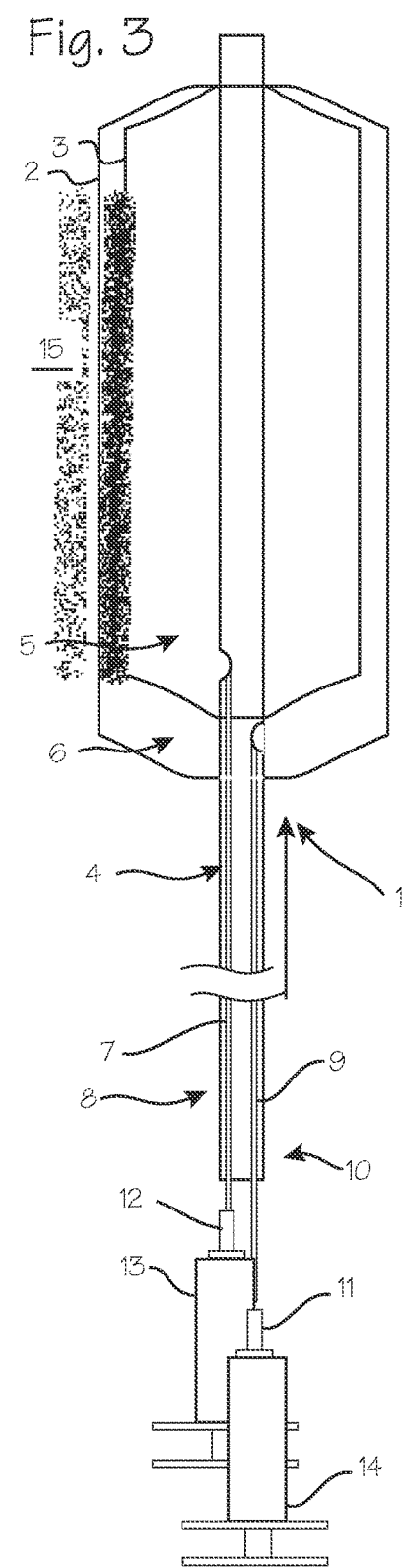

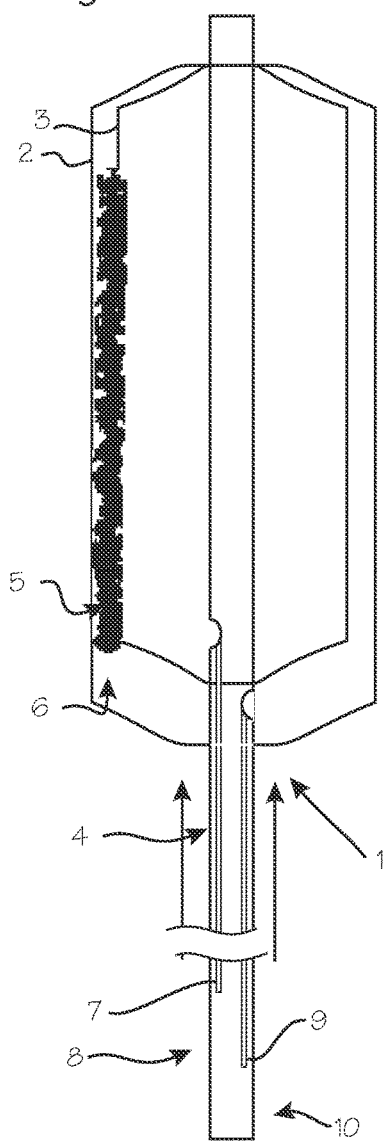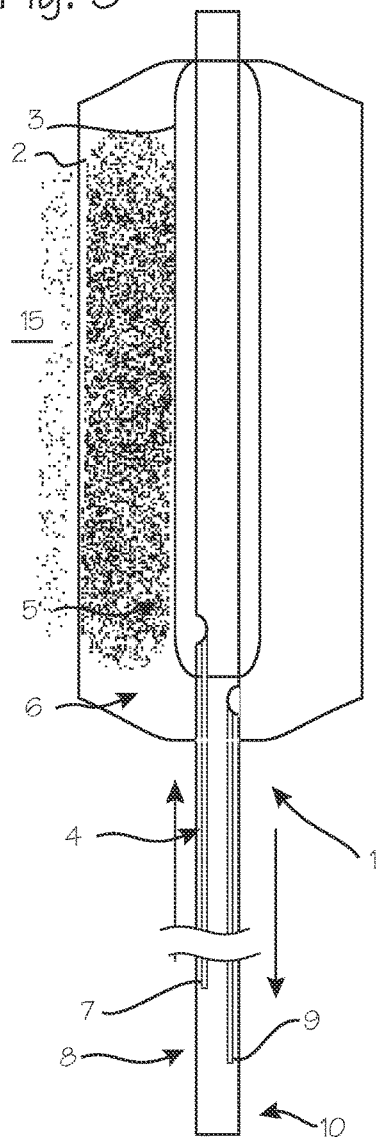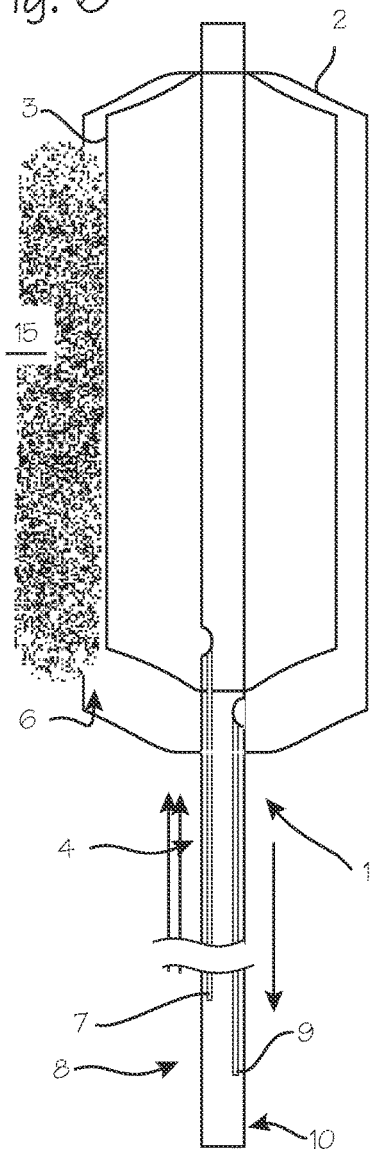

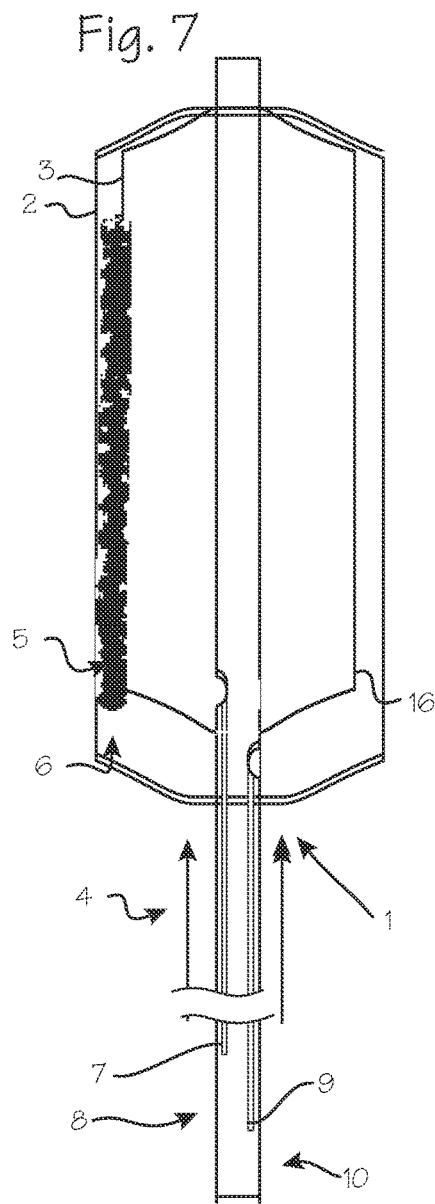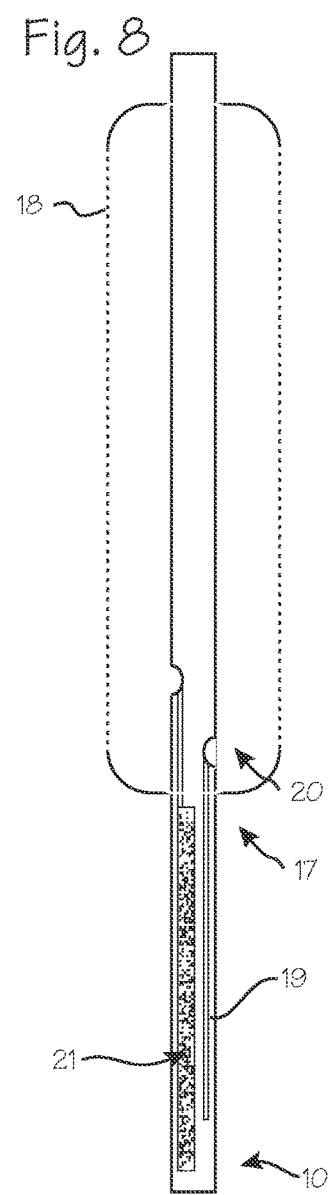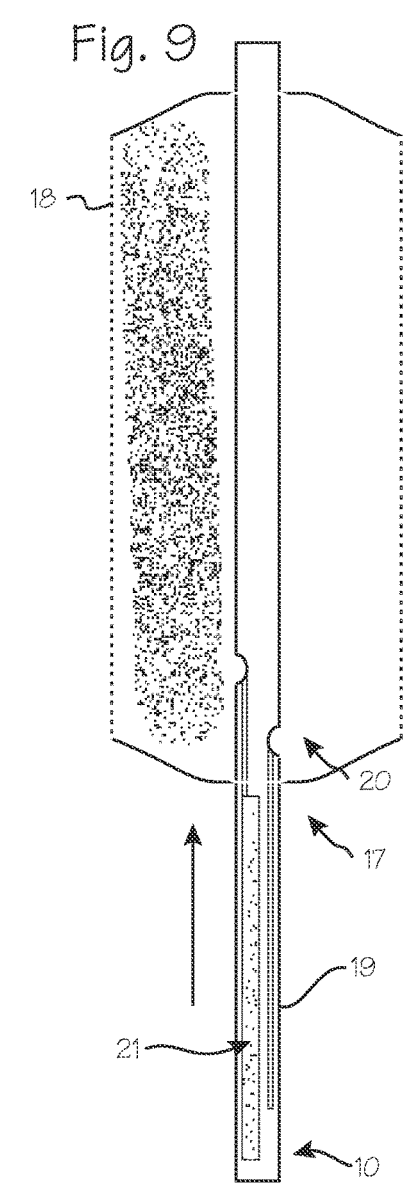

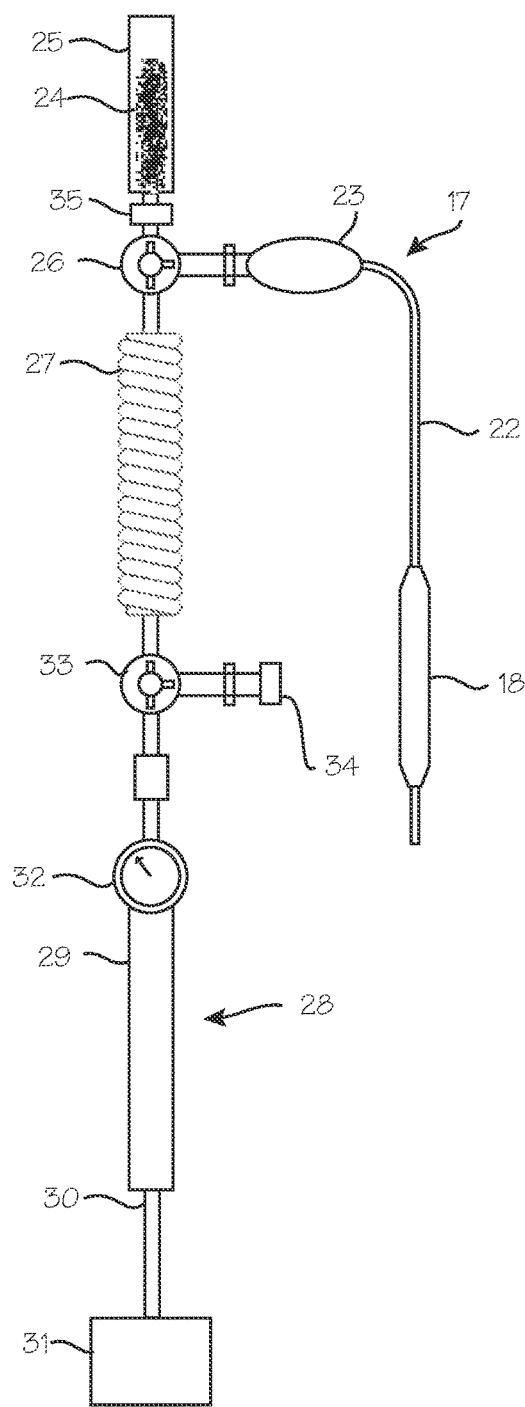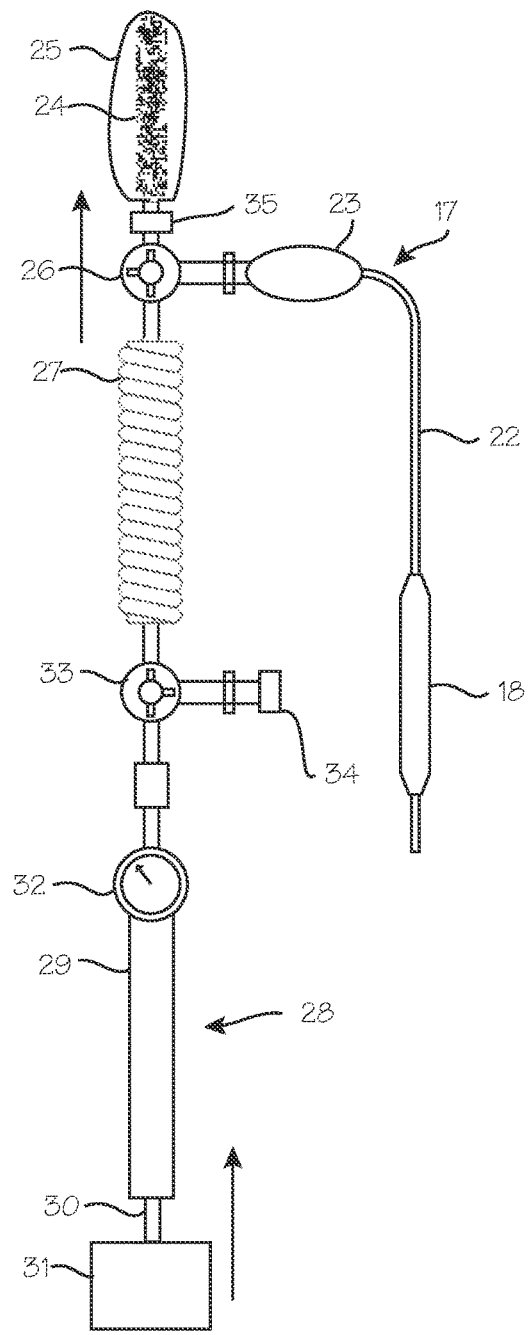

BALLOON CATHETER SYSTEMS FOR DELIVERY OF DRY DRUG DELIVERY VESICLES TO A VESSEL IN THE BODY

This application is a continuation of U.S. application Ser. No. 17/075,080, filed Oct. 20, 2020, which is a continuation of U.S. application Ser. No. 16/115,467, filed Aug. 28, 2018, now U.S. Pat. No. 10,806,909 which is a continuation of U.S. application Ser. No. 15/594,055, filed May 12, 2017, now U.S. Pat. No. 10,207,084, which is a continuation of U.S. application Ser. No. 15/078,940, filed Mar. 23, 2016, now U.S. Pat. No. 9,649,479, which is a continuation of U.S. application Ser. No. 14/247,057, filed Apr. 7, 2014, now U.S. Pat. No. 9,649,478, which is a continuation of U.S. application Ser. No. 12/982,760, filed Dec. 30, 2010, now U.S. Pat. No. 8,696,644, which claims priority to Provisional Patent Application 61/291,345 filed Dec. 30, 2009. U.S. application Ser. No. 14/247,057, filed Apr. 7, 2014, now U.S. Pat. No. 9,649,478, is also a divisional of U.S. application Ser. No. 13/855,653, filed Apr. 2, 2013, now U.S. Pat. No. 8,715,230, which is a continuation of U.S. application Ser. No. 12/982,760, filed Dec. 30, 2010, now U.S. Pat. No. 8,696,644.

FIELD OF THE INVENTIONS

The inventions described below relate to the field of treatment of vascular disease, and more specifically to the field of drug eluting balloons for the treatment of restenosis.

BACKGROUND OF THE INVENTIONS

In the field of vascular disease, restenosis refers to the re-growth of tissue within a blood vessel which has been treated with angioplasty or stent placement, such that the blood vessel becomes occluded shortly after pre-existing blockages are cleared. Whether blood vessels are treated with angioplasty alone, bare metal stents or drug eluting stents, restenosis is likely. To combat restenosis, various compounds have been applied to treated blood vessel walls at the time of initial treatment. These compounds includes rapamycin and paclitaxel and various derivatives of these compounds. Typically, these compounds are delivered to the blood vessel wall through balloons or through a drug-eluting compound on the stent. Drug-eluting stents appear to forestall restenosis, and late term thrombosis is a significant complication of drug eluting stents which must eventually be treated, perhaps with balloon delivery of additionally therapeutic agent. Balloon delivery through various mechanisms has been proposed, including (1) coating balloons with a therapeutic compound and then inflating them within a lesion to press the therapeutic compound into contact with the surrounding blood vessel wall and (2) passing a therapeutic compound through the porous wall of a balloon while the balloon is inflated within the lesion in order to infuse the therapeutic compound into the blood vessel wall. For compounds such as paclitaxel, these techniques appear useful at least to the extent that clinical experimentation is warranted. However, due to inherent properties of rapamycin and its analogs or derivatives, e.g. hydrophobicity, direct delivery of these drugs from amorphous or crystalline coatings on the surface of an angioplasty balloon is inefficient.

SUMMARY

The devices and methods described below provide for effective balloon delivery of rapamycin and other hydrophobic compounds to the wall of blood vessels. Balloon catheters, such as those used for balloon angioplasty, are modified with the addition of a mass of dry micelles, disposed at a suitable location within the balloon or catheter. Immediately prior to use, or during use, the mass of dry micelles is reconstituted with the addition of an aqueous solution into the catheter. The balloon is then pressurized and the reconstituted micelles are forced out of the balloon through a porous wall of the balloon. The dry micelle reservoir may be a powdered lyophilized micelle reservoir or a film, and it can be installed in the balloon catheter during manufacture of the balloon or after manufacture. The reservoir may be installed within the angioplasty balloon, or within a lumen in communication with the angioplasty balloon, or in a storage chamber at the proximal end of the catheter, either as a loose or packed powder or as a film coating. In addition, the dry micelles may be suspended in hydrogel or other stabilized non-aqueous media. The dry micelles are reconstituted and mobilized when wetted by injecting an aqueous solution into the catheter, either during the process of preparing the balloon catheter for use, or during actual use. The micelles are infused into tissue surrounding the balloon when pressurized fluid within the balloon leaks through the wall of the balloon. In a more basic embodiment, a balloon catheter can be provided with a coating of micelles, in dry, reconstituted or original form on the outer surface of a porous balloon wall.

BRIEF DESCRIPTION OF THE DRAWINGS

FIG. 1 illustrates a double-walled balloon catheter with a reservoir of dry micelles.

FIGS. 2 and 3 illustrate a method of operating the balloon catheter of FIG. 1.

FIGS. 4, 5 and 6 illustrate a method of operating the balloon catheter of FIG. 1.

FIG. 7 illustrates a double-walled balloon catheter with the reservoir of dry micelles, in which both the inner and outer balloons are porous balloons.

FIGS. 8 and 9 illustrate a balloon catheter system in which a reservoir of micelles is disposed within a balloon inflation lumen.

FIGS. 10, 11, 12 and 13 illustrate a balloon catheter system with a proximally located micelle reservoir.

DETAILED DESCRIPTION OF THE INVENTIONS

Figure 12:
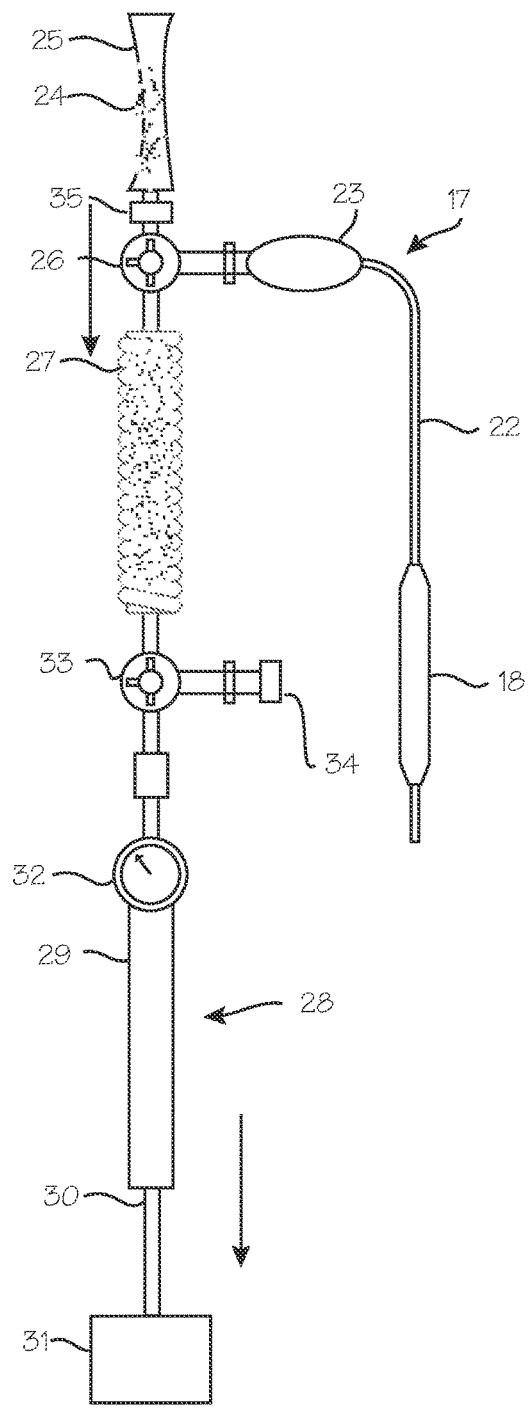

FIG. 1 illustrates a double-walled balloon catheter 1 with a porous walled outer balloon 2 disposed over an inner balloon 3 (which may be porous or non-porous) mounted on the distal end 4 of the catheter, and a reservoir 5 of dry micelles within the balloon catheter, disposed between the inner and outer balloons in the inter-balloon space 6. The dry micelles may be deposited in a reservoir without substantial additional media, or may be suspended in a dry hydrogel or other stabilized non-aqueous media. Within the catheter body, a first lumen 7 communicates from the proximal end 8 to the inner balloon 3, and a second lumen 9 communicates from the proximal end of the catheter to the space between the inner balloon and outer balloon. The porous outer balloon may comprise standard balloon materials such as nylons, block co-polymers (PEBAX), urethanes, PET, PE (HMWPE, LLDPE, etc.), with numerous pores in the size range of 100 to 5000 nm (0.1 to 5 microns), and may be compliant (elastomeric and conformable to the vessel wall) or non-compliant, while the inner balloon may be non-porous or porous, and also may be elastomeric and conformable to the vessel wall (or outer balloon) or non-compliant, though at least one of the inner or outer balloons is preferably non-compliant for devices intended for angioplasty. For angioplasty, the balloon is preferably nylon, about 20 microns thick (0.8 mil thick), with holes 2 to 5 microns in average diameter (measured on the inside surface of the balloon), up to 100 holes of 5 micron diameter or up to 200 holes of 2 micron diameter (or a mix of variously sized holes), an overall length of 20 mm and an expanded diameter of 3 mm. For other purposes, such as treatment of peripheral blood vessels, the balloon may range from 1.5 to 28 mm in diameter and 5 mm to 200 mm or more. The proximal end 10 of the catheter includes the Luer fittings 11 and 12, in fluid communication with the inner balloon and outer balloon, respectively, and reservoirs 13 and 14 which are filled with a physiologically acceptable aqueous solution such as saline, ringers solution or PBS, contrast media (ULTRAVIST® for example) and distension media such as dextran, or other common pharmaceutical excipients such as polypeptides or polysaccharides.

In use, after preparing the balloon catheter and patient, the balloon catheter is navigated to a target site within the patient's vasculature and inflated in order to open an occlusion or restriction at the target site. As illustrated in FIGS. 2 and 3, the outer balloon may be pressurized to several atmospheres of pressure, through the inflation lumen 9 aligned with space between the outer balloon and the inner balloon. This inflation will fill the inter-balloon space 6 with aqueous solution, exerting pressure sufficient to force an occluded target site open, while also creating an environment in which the micelle preparation in micelle reservoir 5 is reconstituted or and the micelles within the preparation are mobilized. During this step, a small portion of the micelles may be forced from the catheter, as illustrated by the diffuse mass 15 of micelles shown outside the outer balloon. After angioplasty (or stent deployment) has been performed to the satisfaction of the interventionalist, while maintaining pressure within the outer balloon (which can be accomplished by blocking the proximal Luer fitting with a small valve) to prevent back leakage of the fluid in the outer balloon, the inner balloon is inflated slowly to force the micelles and fluid out of the outer balloon through the porous wall of the outer balloon, as shown in FIG. 3. Pressure may be maintained for a minute or two (for coronary arteries) or for several seconds to a few minutes (in the peripheral arteries) in embodiments in which the balloons are non-perfusing (that is, the balloon does not allow blood flow to flow past the balloon while inflated), and even longer when the catheter system is embodied in a perfusing balloon system, to force many of the micelles from the reservoir 5 into the blood vessel, as represented by the diffuse mass of micelles 15.

In an alternative method of use, the inner balloon may be used as the balloon which is pressurized to affect the angioplasty or stent deployment as illustrated in FIGS. 4, 5 and 6. In this case, as shown in FIG. 4, the vascular surgeon will inflate the inner balloon through inflation lumen 7, leaving the micelle reservoir dry and intact. After angioplasty (or stent deployment) has been performed to the satisfaction of the vascular surgeon or interventionalist, the vascular surgeon will deflate the inner balloon, as shown in FIG. 5, and fill the outer balloon with sufficient aqueous solution to reconstitute the micelle preparation and mobilize or suspend the micelles. Some micelles may be flushed from the outer balloon at this point. As shown FIG. 6, while maintaining pressure within the outer balloon to prevent back-leakage of the fluid in the outer balloon, the vascular surgeon will re-inflate the inner balloon 3 to force the micelles and fluid out of the outer balloon through the porous wall of the outer balloon.

FIG. 7 illustrates a double-walled balloon catheter with the reservoir of dry micelles, in which both the inner balloon 16 and outer balloon 2 are porous balloons. Using the catheter of FIG. 7 configured with a porous inner balloon, the inner balloon may be used as the balloon which is pressurized to affect the angioplasty or stent deployment. In this case, the vascular surgeon will inflate the inner balloon 3 through inflation lumen 7, and leakage of solution from the inner balloon to the inter-balloon space 6 and the micelle reservoir will wet and mobilize the micelles. The continued pressurization of the inner balloon to accomplish the angioplasty or stent expansion will result in flow of aqueous solution through the porous inner balloon, through the space between the balloons and through the porous wall of the outer balloon, thus carrying micelles out of the catheter and into contact with the blood vessel walls.

Though pre-inflation of balloon catheters is not universally encouraged, the catheter may be prepared, prior to insertion into the vasculature of a patient by filling the catheter with an aqueous solution, such as saline (or ringers solution, contrast media (ULTRAVIST® for example) and distension media such as dextran), and removing any excess solution from the catheter by drawing back fluid through the inflation port. This may include drawing a substantial amount of the micelles from the catheter into a syringe, mixing the aqueous solution and micelles within the syringe outside the catheter, and re-injecting the micelle/aqueous solution mixture into the catheter. The outer balloon may be filled for a period of time to allow reconstitution, and then drained through the inflation lumen (the process may result in drawing some of the micelles into the inflation lumen). If pre-inflation is performed by the vascular surgeon, any of the three methods described above may be used.

FIGS. 8 and 9 illustrate a balloon catheter with a micelle reservoir disposed within an inflation lumen. The catheter 17 includes a balloon 18, which has porous walls and is comparable to the outer balloon of FIG. 1, and an inflation lumen 19 in communication with the balloon volume 20 and an inflation port at the proximal end of the catheter. The micelle reservoir 21 is disposed with the inflation lumen 19, coated on the walls of the lumen or disposed in an enlarged segment of the lumen which can serve as a mixing chamber. Although illustrated in the inflation lumen near the distal end of the balloon, the reservoir may be located more proximally in the inflation fluid pathway, including the inflation lumen, the inflation pathway in the handle of the catheter, or in a separate chamber attached to the proximal handle, between the inflation lumen (or a secondary lumen) and the inflator used to inflate the balloon. In this device, flow of inflation fluid serves to wet and mobilize the micelles, which are then entrained in the inflation fluid and carried into the balloon, as shown in FIG. 9, and then out through the pores of the balloon with that portion of inflation fluid which escapes the balloon. In this embodiment, an inner balloon can also be provided as illustrated in FIGS. 4 through 6, and inflated to force much of the fluid and entrained micelles through the walls of the balloon 18.

FIG. 10 illustrates a balloon catheter system with a proximally located micelle reservoir. In this configuration, the catheter 17 includes the catheter body 22, handle 23, and a balloon 18, which has porous walls and is comparable to the outer balloon of FIG. 1. The micelle reservoir 24 is disposed within a micelle storage chamber 25, in fluid communication with the balloon catheter lumen (within catheter 17) through the three-way valve 26. Opposite the micelle storage chamber 25, the three-way valve communicates with the coiled tube suspension chamber 27. The coiled tube suspension chamber is disposed between the three-way valve 26 and the balloon inflation device 28 (sometimes referred to as an endoflator). The inflation device is a finely calibrated syringe with a chamber 29, plunger 30 and plunger handle 31 operable to draw fluid into the chamber and force fluid from the chamber. The inflator includes a meter 32 which accurately displays the pressure of fluid, and the amount of fluid, injected into the balloon catheter. The three-way valve 26 is operable to selectively align the coiled tube chamber, and the inflator, with the drug delivery lumen within the catheter 17 or the micelle storage chamber 25. A second three-way valve 33 is disposed between the coiled tube suspension chamber 27 and the inflator 28. The inflator may be filled from a fluid source connected to the second three-way valve. A pressure relief valve 34 may be provided to avoid over-pressurization of the system. A filter 35 may be provided at the proximal end of the catheter, at the output of the micelle storage chamber, at the output of the three-way valve (between the three-way valve and the catheter body) or between the coiled tube micelle chamber and the three-way valve 26, to prevent any agglomeration of micelles from passing into the catheter and ensure that only small particles are passed into the balloon. The filter is preferably a static 0.45 micron filter, but may be as small as a 0.1 micron (100 nanometer). The micelle storage chamber 25 is preferable collapsible, so that withdrawal of the micelles after injection of reconstituting fluid is facilitated. The micelle storage chamber may be a collapsible pouch, a cylinder with an easily movable base, or a syringe which must be operated in tandem with the inflator to push the reconstituted suspension from the chamber as the inflator is used to withdraw the suspension. The micelle storage chamber may include a relief valve or vent to enable degassing and facilitate filling. The micelle storage chamber 25 is preferably transparent, so that complete reconstitution and emptying into the coiled tube suspension chamber can be visually confirmed. The coiled tube chamber has an inner diameter of 1 to 2 mm, and a length of about 300 mm. Limiting the diameter to 2 mm or less severely minimizes the mixing or osmosis of micelles into the inflator fluid, so that the concentration of the suspension in the coiled tube chamber is not diluted when inflator fluid is forced into the coiled tube chamber. The coiled tube chamber is coiled merely for compactness. The overall inner volume of the coiled tube is preferably 1 to 2 ml volume of micelle suspension. (The coiled tube suspension chamber and the micelle storage chamber are thus distinguished by their separate functions and distinct structure. The micelle storage chamber is used to store the micelles for extended periods prior to use (after manufacture, in shipping and storage for the shelf life of the micelles formulation in its lyophilized condition). The coiled tube suspension chamber is used intra-operatively, to briefly store the micelles suspension immediately prior to delivery through the catheter and balloon, and is sized and dimensioned to limit mixing of the suspension with the inflator fluid held in the inflator chamber, which it abuts at the boundary of the suspension bolus and the inflation fluid.)

Thus, FIGS. 10 through 13 show a balloon catheter system for delivery of drugs or therapeutic agents to a blood vessel from a dry reservoir stored at the proximal end of the catheter. The balloon catheter comprises a catheter body with a distal end adapted for insertion into the vasculature of a patient, a porous balloon disposed on the distal end. The proximal end of the balloon catheter has a lumen extending from the proximal end to the balloon. The proximal end is adapted for connection to a fluid source. The system also includes a storage chamber with a reservoir of dry drug delivery vesicles, and an inflator and suspension chamber in fluid communication with an inflator. These components are selectively aligned in fluid communication with each other through a valve operable to selectively connect the storage chamber to the suspension chamber or the lumen of the catheter. The inflator is operable to fill the storage chamber with fluid to reconstitute the dry drug delivery vesicles into a fluid suspension of drug delivery vesicles and draw the fluid suspension into the suspension chamber, when the valve is positioned to connect the storage chamber to the suspension chamber, and the inflator is operable to force the suspension from the suspension chamber through the catheter lumen and porous balloon to the blood vessel.

Figure 13:
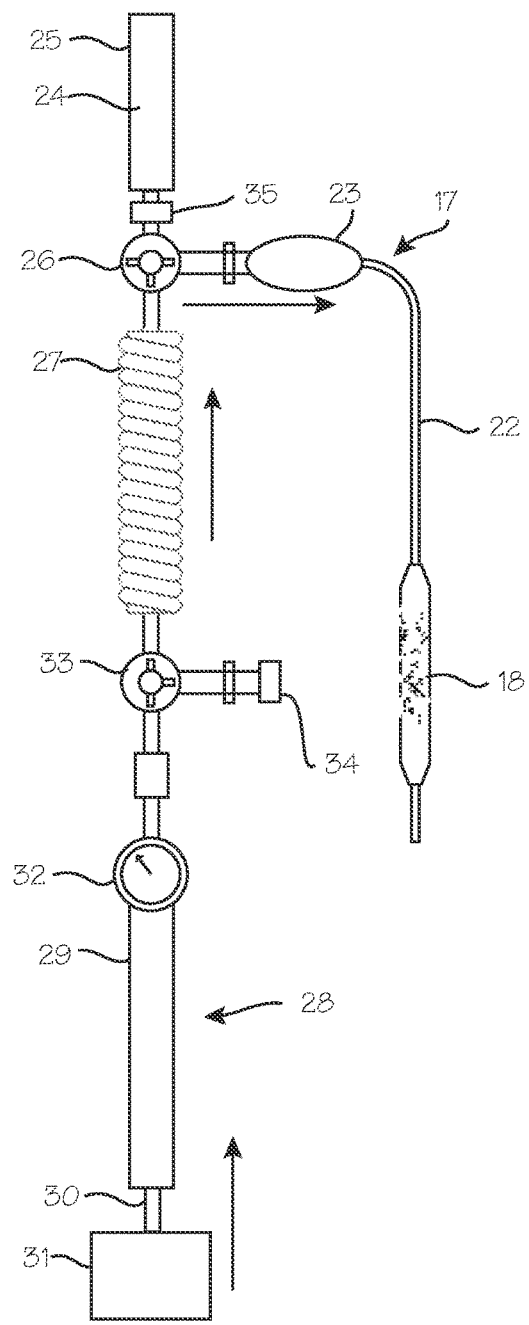

In use, the system of FIG. 10 is operated in several steps. After standard preparation of the catheter, which may include flushing the catheter with water or saline, the operator fills the inflator chamber with fluid, and fills the coiled tube suspension chamber with fluid. As shown in FIG. 11, the operator turns the three-way valve 26 to align the inflator and coiled tube suspension chamber 27 with the micelle storage chamber 25, and forces the fluid into the micelle storage chamber 24 by operating the inflator handle. The micelle storage chamber is depicted in a distended state, to illustrate that it has been filled with fluid. Filling the micelle storage chamber with fluid will reconstitute the micelles in the micelle storage chamber and create a suspension that can be moved into the catheter. Next, as shown in FIG. 12, the three-way valve 26 is maintained in position to align the inflator and coiled tube suspension chamber 27 with the micelle storage chamber 25, and the suspension of micelles in a small bolus 36 is drawn into the coiled tube suspension chamber 27. (The micelle storage chamber 25 is depicted in a collapsed state, to illustrate that its contents have been withdrawn.) Routine steps are then taken to ensure that no gas is entrained in the micelle suspension. Next, as shown in FIG. 13, the three way valve is manipulated to align the coiled tube suspension chamber and inflator with the catheter lumen, and the operator pushes the inflator handle into the inflator chamber to force additional fluid into the coiled tube suspension chamber and through to the catheter. The suspension that had been drawn into the coiled tube suspension chamber 27 (FIG. 12) is pushed, in a substantially intact bolus 36, into the catheter and thus into the balloon. If not already flushed of air, this step may serve to flush the catheter and balloon prior to insertion into the body and navigation into the blood vessel to be treated. When flushed, the catheter is inserted into the vasculature and navigated to the blood vessel to be treated. The operator continues to pressurize the inflator, and thus pressurize the balloon, as necessary to force the suspension, and the suspended micelle formulation, through the wall of the balloon and into body tissue surrounding the balloon. The delivery of fluid can continue until inflation fluid (from the inflator, which may be a contrast fluid) exits the balloon. The inflation fluid, or a flushing fluid delivered using the inflator, preferably includes contrast agent (iodinated radiocontrast agents, e.g. ionic agents like diatrizoate or metrizoate or non-ionic agents like iopamidol, iopromide, or iodixanol) so that the arrival of the inflation fluid at the balloon pores, and thus complete ejection of the micelle suspension, can be visually confirmed under fluoroscopy.

Figure 14:
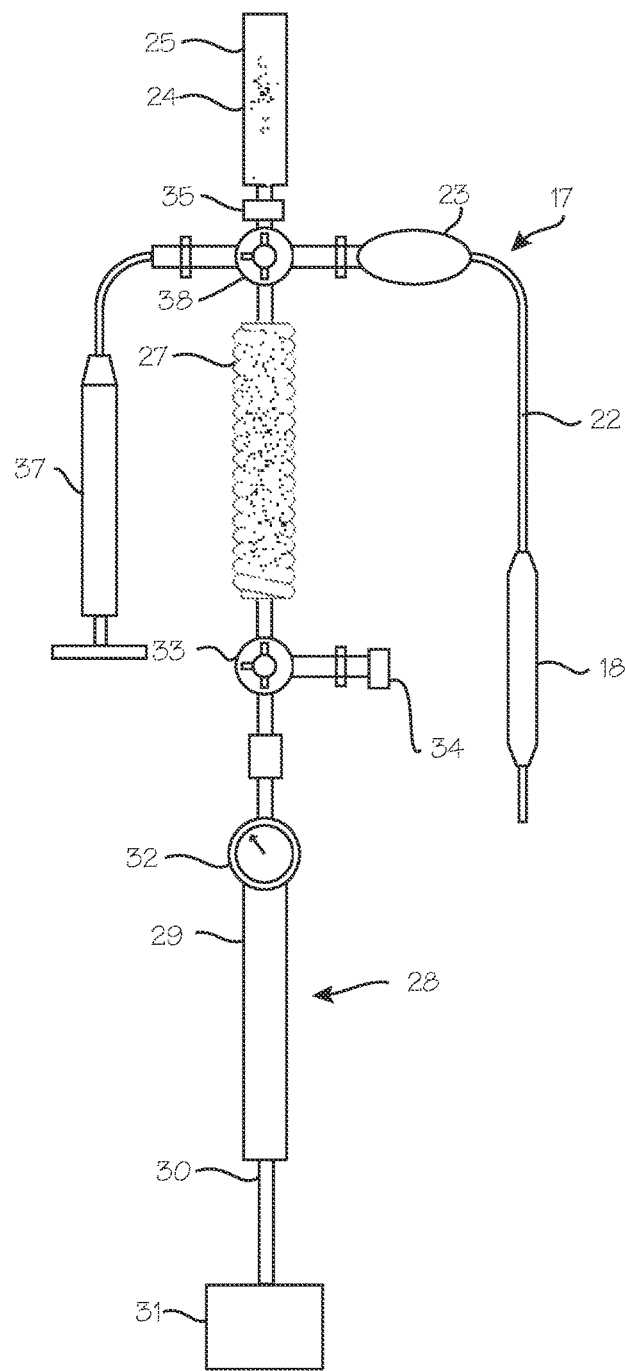
FIG. 14 illustrates an alternative method of wetting the dry micelle formulation in the system of FIGS. 10 through 13.

The method may be modified by injecting fluid into the micelle storage chamber from a syringe separate from the inflator, as shown in FIG. 14, which shows the micelle reservoir 24 within the micelle storage chamber 25, catheter 17, the coiled tube suspension chamber 27, the balloon inflation device 28 and its chamber 29, plunger 30, plunger handle 31, meter 32 and the second three-way valve 33 as in FIG. 10, and the additional syringe 37 may be provided, and connected to the micelle storage chamber through the four-way valve 38. In this system, the four-way valve 38 is positioned to align the syringe in fluid communication with the micelle storage chamber, then the syringe is operated to fill the micelle storage chamber with fluid and the four way valve is then turned to align the coiled tube suspension chamber 27 to the micelle storage chamber, and operation is thereafter performed as described in relation to FIGS. 10 through 13. Other means for filling the micelle storage chamber with reconstituting fluid may be used, included injection through a self-sealing membrane in the chamber wall, a needle port, or the like.

Figure 15:
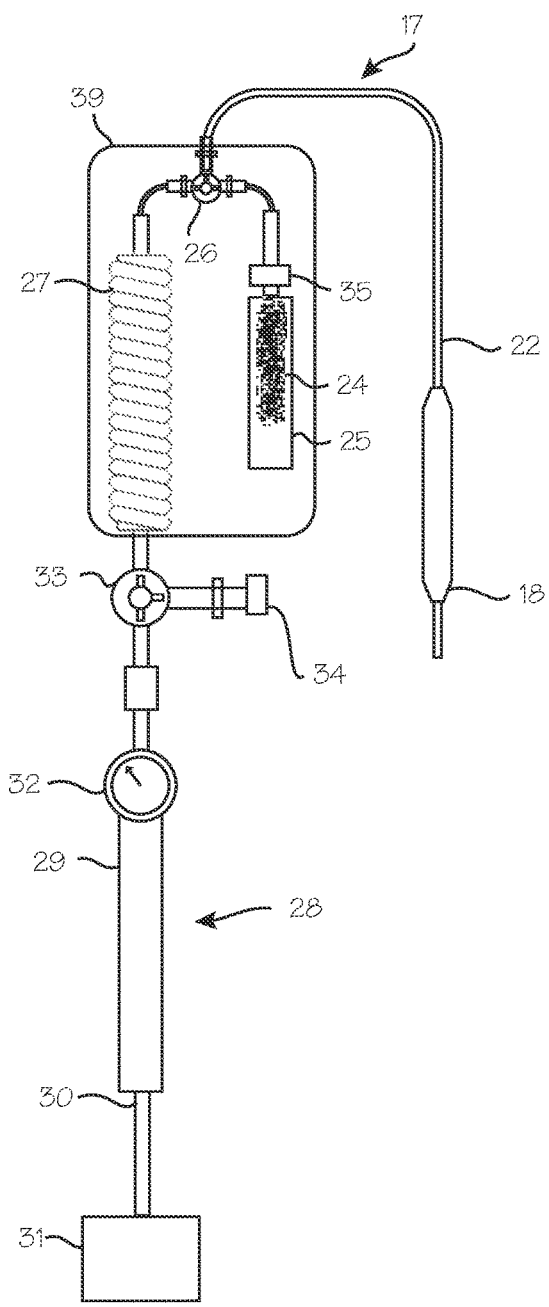
FIG. 15 illustrates a balloon catheter system in which the reservoir of micelles is disposed within a proximal storage chamber within the catheter handle.

The proximal components of the system, including the micelle chamber, coiled tube suspension chamber, filter and three-way valve, may be provided in a single housing to facilitate handling and operation of the system. This is illustrated in FIG. 15, which shows the micelle storage chamber 25 and coiled tube isolation reservoir 27 and, optionally, the three-way valve 26 disposed in the handle 39. This configuration provides a conveniently operable system with the micelle reservoir stored within the handle of the catheter to be used to deliver the micelle formulation to the body through the balloon. The system is assembled after the micelle formulation is filter sterilized and deposited in the micelle storage chamber. After the micelle storage reservoir is installed in the handle and sealed to the valve, the entire catheter may be sterilized with standard ETO sterilization or other methods that would otherwise degrade the micelle formulation.

Figure 16:
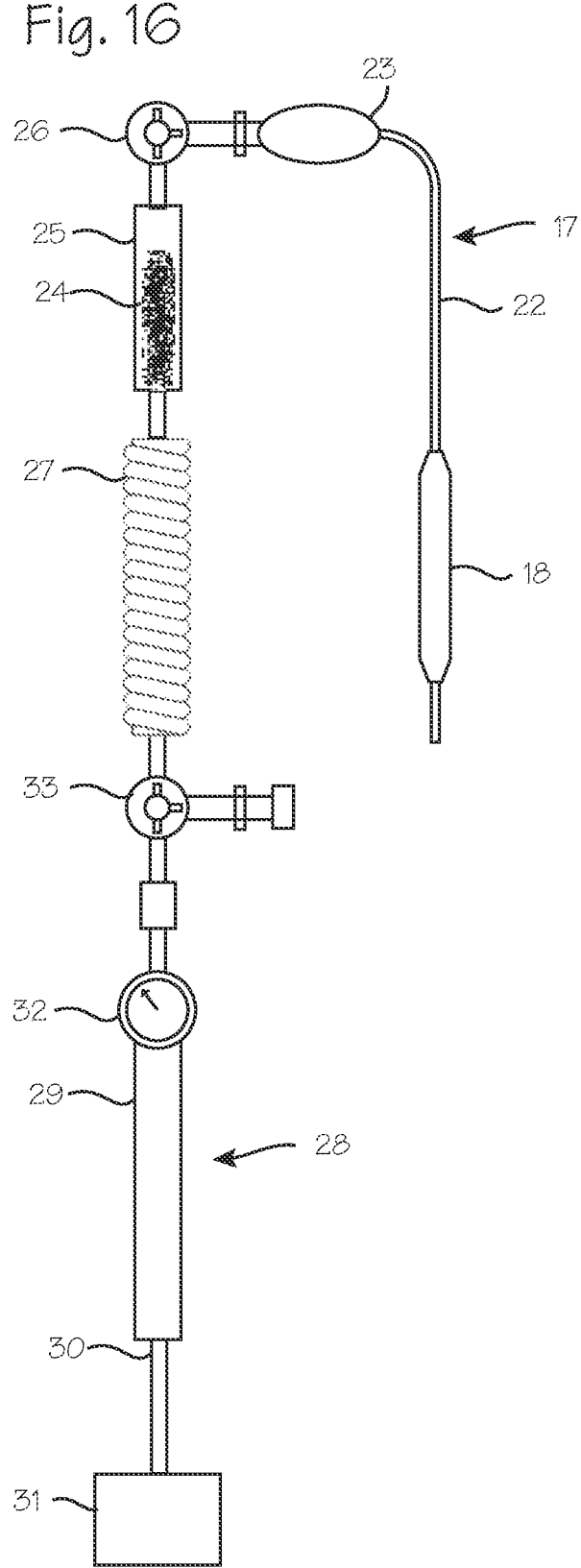
FIG. 16 illustrates the system of FIGS. 10 through 13 modified by placement of the micelle storage chamber between the three-way valve and the coiled tube chamber.

The system may be modified by placing the micelle storage chamber between the three-way valve and the coiled tube chamber, as shown in FIG. 16, which shows the micelle reservoir 24 within the micelle storage chamber 25, catheter 17, the coiled tube suspension chamber 27, the balloon inflation device 28 and its chamber 29, plunger 30, plunger handle 31, meter 32 and the second three-way valve 33 as in FIG. 10. In this system, the micelle storage chamber is positioned between the three-way valve and the coiled tube chamber. The inflator is operated to fill the micelle storage chamber with fluid and withdraw the resulting suspension into the coiled tube chamber, and operation is thereafter performed as described in relation to FIGS. 10 through 13.

Referring again to the system of FIGS. 10 through 13, the purpose of the coiled tube suspension chamber is to expose the suspension bolus to the pneumatic force of the inflation fluid in the inflator while minimizing mixing. Mixing can also be prevented by replacing the coiled tube with a second cylinder divided into chambers by a piston. In such an embodiment, a first chamber, in fluid communication with the three-way valve 26 and the micelle storage chamber 25, is filled with reconstitution fluid, and the second chamber, closest to the inflator, is filled with fluid and is in fluid communication with the inflator. Operation of the inflation to force the piston back and forth serves to force the reconstitution fluid into the micelle storage reservoir, and withdraw the resulting suspension into the cylinder, and thereafter force the suspension from the first chamber into the catheter with pneumatic pressure applied to the piston from the inflator. To accomplish the goal of flushing all the suspension, and also the goal of providing the contrast bloom that confirms complete delivery, the inflator provides inflation fluid or contrast through a bypass communication around the cylinder to the catheter lumen.

The inflation pressure and inflation duration, in combination with the amount of dry micelle formulation and volume of the reconstituted micelle suspension can be controlled to ensure a predetermined dose of micelles, and encapsulated drug, are delivered to the body tissue surrounding the balloon. Pressure applied by the inflator may be two to twenty atmospheres, and the inflator is preferably operated to apply 6 to 12 atmospheres of pressure. With suspended micelle formulation in the suspension chamber, and hole sizes of 2 to 5 microns in the balloon, application of 12 atmospheres for 60 seconds will deliver the entire 1 ml of the suspended micelle formulation through the catheter and balloon wall. The parameters may be adjusted to achieve 0.25 to 10 ml over the course of 10 to 120 seconds. The dosage of drug or therapeutic agent actually delivered can thus be controlled and predetermined with some certainty by controlling the amount of drug or therapeutic agent in the micelle formulation disposed in the micelle storage chamber. For example, if it is desired to deliver 2 mg of rapamycin to a diseased portion of a blood vessel, the micelle reservoir containing 2 or 3 mg of rapamycin can be stored in the micelle storage chamber, reconstituting the micelles with fluid to achieve a concentration of 2 mg/ml (that is, 1 ml if the micelle storage chamber contains 2 mg total rapamycin), withdrawing 1 ml of fluid into the coiled tube suspension chamber, and forcing the entire 1 ml through the catheter and balloon into the blood vessel walls.

The micelles used in the catheter systems described above may be formulated and lyophilized using known procedures, or procedures developed in the future. The micelle reservoir may be disposed within the catheter after formulation and lyophilization, or they may be installed in an aqueous slurry in the catheter or a catheter component, and lyophilized afterward, whereupon the catheter may be stored for extended periods of time prior to shipment, and wetted just prior to use in a patient, or when the balloon or balloons are inflated within the body of the patient. The micelles may be loaded with rapamycin or other therapeutic agents such as rapamycin analogs, ABT-578, zotarolimus, everolimus, biolimus A9, deforolimus (also referred to as ridaforolimus), temsirolimus, tacrolimus, pimcrolimus, nitric oxide synthase, C3 exoenzyme, RhoA inhibitors, tubulusin, A3 agonists, CB2 agonists, 17-AAG, Hsp90 antagonists, tyrphostins, cathepsin S inhibitors, paclitaxel, dexamethasone, ceramides, dimethyl sphingosine, ether-linked diglycerides, ether-linked phosphatidic acids, sphinganines, estrogens, taxol, taxol analogs, actinomycin D, prostaglandins, vitamin A, probucol, Batimastat, Statins, Trapidil, mitomycin C and Cytochalasin B.

The micelles used in the catheter are preferably formed from tri-block amphiphilic co-polymers of the form A-B-A where A is hydrophobic (PCL (Polycaprolactone) or PLGA (poly(lactic-co-glycolic acid) for example) and B is hydrophilic (PEG, or PEO for example), in which case the A block interacts with the micelle core and drugs encapsulated in the core and the B block forms the shell of the micelle. The micelles may also be formed of tri-block amphiphilic copolymers of the form A-B-A where A is PLA, PDLLA, PPS, PPO, or Poly(amino acid)s and B=PEG or PEO. Tri-block copolymers of the form B-A-B and Di-block copolymers of the form A-B may also be used. Additionally, the micelles may be formed with a core polymer of PCL. The micelles are formed by nano-precipitation, and result in micelle sizes in the range of 40-120 nm diameter. Rapamycin or other drug particles can be loaded into the micelles by entrapment during the initial formation of the micelles. This will result in efficient loading of the drug particles, and a high percentage of the drug particles in the formulation slurry will become entrapped within the micelles. Drug loading may be accomplished by adsorption or migration of the drug into the micelles after formulation, though this is not expected to be as efficient as entrapment. The systems and methods described above can be employed to deliver other small drug delivery vesicles or delivery vessels in addition to micelles, particularly small dry vesicles that benefit from reconstitution immediately prior to delivery, such as nanoparticles and liposomes. Nanoparticles useful in the system include e.g. PCL, PLGA, PLA, PDLLA, PPS, PPO, or Poly(amino acid)s loaded with drugs. Liposomes can include dry powder liposomes made by lyophilization or dry-spraying. The various reservoirs shown in the various devices may be protected by filling the catheter or chamber or balloon housing the reservoir with nitrogen or inert gas.

After formulation, the micelles are freeze-dried, or lyophilized. The micelles may survive intact, or partially collapse into other structures. Nonetheless, upon re-wetting, a substantial portion of the micelle population will be mobilized intact. To enhance the survival of the micelles, lyophilization may be performed after a lyoprotectant or cryoprotectant, for example, sucrose, glucose, lactose, mannitol, trehalose, may be added to the original micelle mixture. After lyophilization, the mixture of the micelles, encapsulated drug within the micelles, and the lyoprotectant compound is particularly useful as the reservoir described above.

The micelles used in this system and method described above should be in the range of 40 to 250 nm (0.04 to 0.250 micron) generally, and in the range of 60 to 120 nm when formulated from the tri-block copolymer mentioned above (PLGA-PEG-PLGA or PCL-PEG-PCL). This size will result in a balance of efficient penetration of the micelles into the artery walls and sufficient space within the micelles to encapsulate a suitable amount of rapamycin or other therapeutic substance. Use of tri-block polymers such as PLGA-PEG-PLGA will provide micelles in the desired sized range. For micelle doses prepared prior to loading into the catheter, polydispersity index of the micelle population is preferably less than 0.2, as measured by a dynamic light diffusion test. This may be achieved by controlled formulation, filtration or centrifugation of polydisperse population of micelles.

For reconstitution of the micelles, an aqueous solution, typically an isotonic solution with or without additional lyoprotectant and/or pharmaceutical excipient, is added to the dry micelle formulation via syringe, catheter barrel, or tube. The suspension is further mixed, if required, by physical agitation, drawing back and forth into a syringe, or other means.

While the devices and methods described above have been illustrated in the context of coronary artery treatment and restenosis, they may be used in other vessels in the body, including the peripheral blood vessels, esophagus, ureters, urethra, sinus, valves, etc., and may be used to deliver a variety of drugs, therapeutic agents, especially hydrophobic agents which may be encapsulated in micelles or liposomes.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method for treating a coronary artery of a patient, comprising the steps of:
   providing a catheter system comprising:
   a balloon catheter comprising a catheter body with a distal end adapted for insertion into vasculature of a patient, a porous balloon disposed on the distal end, a proximal end adapted for connection to a fluid source, and a lumen extending from the proximal end to the balloon;
   a storage chamber with a reservoir of dry drug delivery vesicles;
   an inflator;
   a suspension chamber in fluid communication with the inflator;
   a valve operable to selectively connect the suspension chamber to the storage chamber or to the lumen of the catheter; wherein
   said suspension chamber comprises a cylinder divided into two cylinder chambers by a piston, with a first of the cylinder chambers aligned for fluid communication with the valve and the storage chamber and a second of the cylinder chambers in fluid communication with the inflator;
   operating the valve to align the first cylinder chamber with the storage chamber;
   forcing fluid from the first cylinder chamber into the storage chamber to reconstitute the drug delivery vesicles in the storage chamber and create a suspension of reconstituted drug delivery vesicles;
   using the inflator, drawing the suspension of drug delivery vesicles into the first cylinder chamber;
   operating the valve to align the first cylinder chamber with the lumen of the catheter; and
   navigating the distal end of the catheter to the coronary artery and inflating the balloon to affect stent deployment of a stent in the coronary artery;
   operating the inflator to force additional fluid into the second cylinder chamber, to thereby force the suspension of drug delivery vesicles from the first cylinder chamber into the catheter, thereby forcing the suspension of drug delivery vesicles through a wall of the balloon and into the coronary artery proximate the balloon.

2. The method of claim 1, wherein the drug delivery vesicles comprise micelles loaded with rapamycin or rapamycin analogs.

3. The method of claim 2 wherein: the porous balloon has pores of predetermined size; the step of reconstituting the micelles is performed to obtain micelles of a size; wherein the predetermined size of the pores is 2 to 50 time the size of the micelles.

4. The method of claim 2 wherein: the porous balloon has pores of predetermined size; the step of reconstituting the micelles is performed to obtain micelles of a size; wherein the predetermined size of the pores is 2.5 to 125 time the size of the micelles.

5. The method of claim 1, wherein the porous balloon has pores of predetermined size; the step of reconstituting the drug delivery vesicles is performed to obtain drug delivery vesicles of a size; wherein the predetermined size of the pores is 2 to 50 times the size of the drug delivery vesicles.

6. The method of claim 1, wherein the drug delivery vesicles comprise micelles loaded with ABT-578, zotarolimus, everolimus, biolimus A9, deforolimus, temsirolimus, tacrolimus, pimcrolimus, nitric oxide synthase, C3 exoenzyme, RhoA inhibitors, tubulusin, A3 agonists, CB2 agonists, 17-AAG, Hsp90 antagonists, tyrphostins, cathepsin S inhibitors, paclitaxel, dexamethasone, ceramides, dimethyl sphingosine, ether-linked diglycerides, ether-linked phosphatidic acids, sphinganines, estrogens, taxol, taxol analogs, actinomycin D, prostaglandins, vitamin A, probucol, Batimastat, Statins, Trapidil, mitomycin C or Cytochalasin B.

7. The method of claim 1, wherein the porous balloon has pores of predetermined size; the step of reconstituting the drug delivery vesicles is performed to obtain drug delivery vesicles of a size; wherein the predetermined size of the pores is 2.5 to 125 times the size of the drug delivery vesicles.

\* \* \* \* \*